July 8, 1952 C. D. CORLISS Plant Pat. 1,112
EUONYMUS PLANT
Filed July 30, 1951
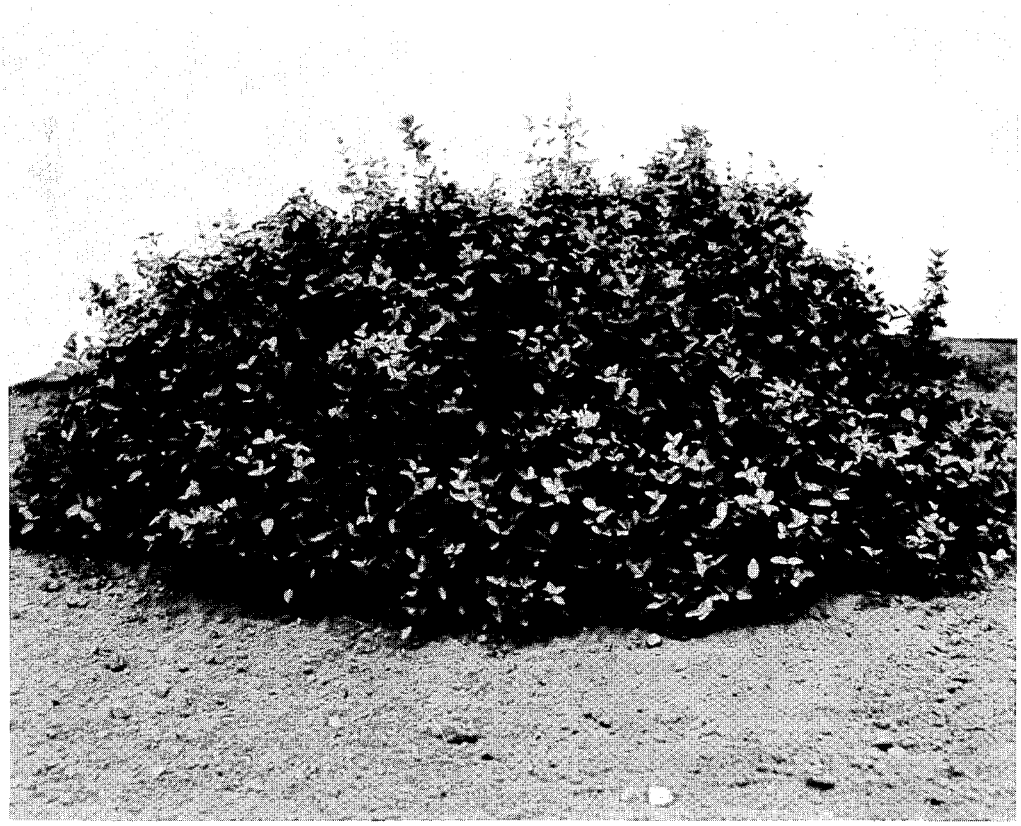
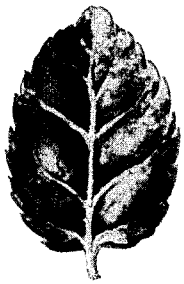
INVENTOR
Clifford D. Corliss
By Orville M. Kile
Plant Patent Agt.

Patented July 8, 1952

Plant Pat. 1,112

UNITED STATES PATENT OFFICE 1,112

EUONYMUS PLANT

Clifford D. Corliss, Gloucester, Mass., assignor to Corliss Bros., Inc., Gloucester, Mass., a corporation of Massachusetts Application July 30, 1951, Serial No. 239,347

1 Claim. (Cl. 47—59)

My present invention relates to a new and distinct variety of evergreen Euonymus shrub originated by me in Gloucester, Massachusetts, as a selected seedling resulting originally from a cross between *Euonymus fortunei* radicans and *Euonymus fortunei* minima, both unpatented, and followed by many years of observation and selection after the cross was made.

This new shrub variety is endowed with new and unusual characteristics which distinguish it from its parents and from all other varieties known to me. It is similar to its minima parent principally in its dwarf type of growth, and to its radicans parent in its leaf structure, although there are other similar characteristics as well as many differences. Leaves differ greatly from those of radicans; whereas radicans leaves are oval, wavy-toothed, and usually dull green with pale veins, leaves of my new variety are ovate to broad ovate and considerably smaller and instead of dull pale green they are dark glossy green on the upper side but with lighter colored veins and under surface.

The plant is a very dwarf shrub—dense, compact and slow-growing—and has a generally low, wide outline, sturdy in character and appearance. Unlike its parent radicans, it is not a vine and has no tendency to trail or climb. Close to its center where the branches touch the ground it has rooted itself in but not in any sense does it have a trailing growth. The great density of its leaves and branches results principally from the presence of a substantially greater number and more closely spaced branches and branchlets. The low, broad, symmetrical shrub shape of the bush is natural without shearing or trimming.

No berries have ever been produced on this variety, although the original plant is now fifteen years old.

The original plant has never been sheared or trimmed and has attained a symmetrical spread of about 3 feet in diameter and is 15 to 18 inches in height.

Due to its strong fibrous root system, my new variety is very easily and successfully transplanted. It is a most versatile and useful hardy broadleaf evergreen shrub that will add great interest and value in landscaping when used in planting low terraces, as a foreground planting in front of taller plants, and for foundation plantings.

This new variety is tolerant of extremely low temperatures having, without winter protection, withstood below-zero weather in northeastern Massachusetts, with no sign of winter burn. It has also shown great drought resistance, having survived two of the driest seasons in recorded history in this vicinity. It is tolerant of either moist or dry locations; to sand, clay or loam soils; and to sun and a considerable degree of shade.

My new variety has been asexually reproduced in large numbers, the reproduction having taken place in northeastern Massachusetts by means of cuttings, with the result that its distinctive characteristics have proved to be permanent.

In the accompanying illustration is shown a bush of this new variety indicating its low, wide natural growth, and, in the lower left-hand corner, a sketch of a single enlarged leaf in approximately its true colors.

In the following description of the plant, color plate designations refer to Ridgway's Color Standards and Nomenclature. Other color names indicate the ordinary dictionary meaning.

Growth habit: Slow-growing, dwarf shrub. Very sturdy.

Form: Dense and compact. Width approximately twice its height.

Density: Branches are more numerous and much more closely spaced than in the parent varieties and are quite uniform in appearance. The foliage is substantially more densely leafed.

Size: The original plant, after fifteen years' growth, has attained a height of 15 to 18 inches and a spread of about three feet.

Leaves:

*Type.*—Evergreen.

*Position.* — Opposite. Leaf blades borne horizontally at right angles to the axis of the stems.

*Size.*—Average 2.5 cm. in length and 1.5 cm. in width.

*Shape.*—Ovate to broad ovate. Margins crenate-dentate, slightly revolute. Apex emarginate.

*Color.*—Upper surface of older leaves is dark, glossy green—Forest Green (Pl. XVII) or darker, but with glossy surface. The veins and under surface are a much lighter green—approximately Biscay Green (Pl. XVII) and without gloss. New leaves are approximately Parrot Green (Pl. VI). It is to be understood that while the colors of typical leaves are approximately as given, no claim is made to color except that the main foliage is dark green as opposed to light green.

*Texture.*—Thin and leathery.

*Petioles.*—Short, approximately .2 mm. long, closely appressed to the stem.

Branchlets: Very closely spaced; minutely warty; light green, approximately Biscay Green (Pl. XVII).

Buds: Inconspicuous; small; elongate-pointed; less than 2 mm. in length.

Bud scales: Imbricated; lighter colored than branchlets.

Flowers and fruit: Lacking.

Having thus disclosed my invention, I claim: The new and distinct variety of evergreen Euonymus plant, substantially as herein shown and described, characterized particularly by its low, wide, compact, thick growth and the great density of its foliage and branchlets; its natural habit of forming a neatly rounded dwarf bush generally twice as broad as tall, as described and illustrated, and of retaining its low, wide shape without shearing or trimming; its dark green leaves with lighter veins and leathery texture; its abundant root system; and its great plant hardiness and drought resistance.

CLIFFORD D. CORLISS.

No references cited.